US00PP12813P2

(12) United States Plant Patent
Gray

(10) Patent No.: US PP12,813 P2
(45) Date of Patent: Jul. 30, 2002

(54) MANDEVILLA PLANT NAMED 'RED VELVET PETITE'

(75) Inventor: John F. Gray, Hawthorne, FL (US)

(73) Assignee: Lake Area Nursery, Hawthorne, FL (US)

( * ) Notice: Subject to any disclaimer, the term of this patent is extended or adjusted under 35 U.S.C. 154(b) by 29 days.

(21) Appl. No.: 09/801,595

(22) Filed: Mar. 8, 2001

(51) Int. Cl.[7] ..... A01H 5/00
(52) U.S. Cl. ..... Plt./232

(58) Field of Search ..... Plt./232

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Mandevilla plant named 'Red Velvet Petite', characterized by its compact growth habit; short internodes; relatively small, glossy, dark green leaves; flowers that are dark pink in color when temperatures are less than 29° C. and intensify to red in color when temperatures are greater than 29° C.; and tolerance to low and high temperatures.

2 Drawing Sheets

BACKGROUND OF THE INVENTION

The present Invention relates to a new and distinct cultivar of Mandevilla plant, botanically known as *Mandevilla hybrid*, and hereinafter referred to by the name 'Red Velvet Petite'.

The new cultivar is a product of a planned breeding program conducted by the Inventor in Hawthorne, Fla. The objective of the breeding program was to develop new compact Mandevilla cultivars with attractive and unique flower colors.

The new cultivar originated from a cross-pollination of the *Mandevilla hybrid* cultivar PSJAM LP1, disclosed in U.S. Plant Pat. No. 10,611, as the female, or seed, parent with an unnamed selection of *Mandevilla hybrid*, not patented, as the male, or pollen, parent in Hawthorne, Fla., in November, 1996. The new cultivar was discovered and selected by the Inventor as a flowering plant within the progeny from this cross-pollination in a controlled environment in Hawthorne, Fla., in 1999. The new cultivar was selected on the basis of its compact growth habit.

Asexual reproduction of the new cultivar by terminal cuttings taken in Hawthorne, Fla, since spring, 2000, has shown that the unique features of this new Mandevilla are stable and reproduced true to type in successive generations.

SUMMARY OF THE INVENTION

Plants of the cultivar Red Velvet Petite have not been observed under all possible environmental conditions. The phenotype may vary somewhat with variations in environment such as temperature, light intensity, daylength, humidity, water status and/or fertilizer rate and type without, however, any variance in genotype.

The following traits have been repeatedly observed and are determined to be the unique characteristics of 'Red Velvet Petite'. These characteristics in combination distinquish 'Red Velvet Pettite' as a new and distinct cultivar:

1. Compact growth habit.
2. Short internodes.
3. Relatively small, glossy, dark green leaves.

4. Flowers that are dark pink in color when temperatures are less than 29° C. and intensify to red in color when temperatures are greater than 29° C.
5. Tolerance to low and high temperatures.

Plants of the new Mandevilla differ primarily from plants of the female parent cultivar PSJAM LP1 in flower color as flowers of plants of the cultivar PSJAM LP1 are light pink in color. In addition, in side-by-side comparisons conducted by the Inventor in Hawthorne, Fla., plants of the new cultivar had smaller leaves and shorter internodes than plants of the cultivar PSJAM LP1. Plants of the new cultivar differ from plants of the male selection primarily in flower color.

Plants of the new Mandevilla can be compared to plants of the cultivar Red Velvet, disclosed in U.S. Plant patent application Ser. No. 09/664,134. In side-by-side comparisons conducted by the Inventor in Hawthorne, Fla., plants of the new Mandevilla had smaller leaves, shorter internodes and smaller and fewer flowers than plants of the cultivar Red Velvet.

Plants of the new Mandevilla can also be compared to plants of the cultivar Alice DuPont, not patented. In side-by-side comparisons conducted by the Inventor in Hawthorne, Fla., plants of the new Mandevilla had smaller leaves, shorter internodes and smaller flowers than plants of the cultivar Alice DuPont. In addition, plants of the new cultivar and the cultivar Alice DuPont differ in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Mandevilla.

The photograph on the first sheet comprises a side perspective view of a typical plant of 'Red Velvet Petite'.

The photograph at the top of the second sheet comprises a close-up view of typical flowers and leaves of 'Red Velvet Petite'.

The photograph at the bottom of the second sheet comprises a close-up view of a typical flower of 'Red Velvet Petite'.

DETAILED BOTANICAL DESCRIPTION

In the following description, color references are made to The Royal Horticultural Society Colour Chart except where general terms of ordinary dictionary significance are used. Plants used for this description were about six to eight months old and grown in one-gallon containers in a clear polyethylene-covered greenhouse in Hawthorne, Fla. during the spring. Day temperatures ranged from 29 to 35° C., and night temperatures ranged from 13 to 18° C.

Botanical classification: *Mandevilla hybrid* cultivar Red Velvet Petite.

Parentage:

*Female, or seed, parent.*—*Mandevilla hybrid* cultivar PSJAM LP1, disclosed in U.S. Plant Pat. No. 10,611.

*Male, or pollen, parent.*—Unnamed selection of *Mandevilla hybrid*, not patented.

Propagation:

*Type cutting.*—Terminal cuttings.

*Time to intiate roots, summer.*—About 21 days at 26° C.

*Time to initiate roots, winter.*—About 30 days at 21° C.

*Time to develop roots, summer.*—About 60 days at 29 to 35° C.

*Time to develop roots, winter.*—About 70 to 80 days at 24° C.

*Root description.*—Numerous, thick, fibrous and freely branching.

Plant description:

*Form.*—Perennial evergreen flowering plant; twining vine; initially upright, then vining, requires support to maintain upright habit. Plants are typically pinched about 3 months after planting to enhance lateral branch development; potentially two lateral branches form at every node.

*Plant height* (*length*).—About 95 cm.

*Plant diameter.*—About 27 cm.

*Vigor.*—Moderately vigorous.

*Lateral branches.*—Length: About 95 cm. Diameter: About 3 mm. Internode length: About 6.3 cm. Shape: Round in cross-section. Aspect: Initially upright, then trailing, requires support. Strength: Flexible, moderately strong. Texture: Very fine, white and dense pubescence. Color: Young stems: Green, 144A. Mature stems: Green, 144A with slight anthocyanin, close to 59A.

*Foliage description.*—Leaves relatively small, simple, generally symmetrical and long-persisting; opposite. Quantity per lateral branch: About 32. Length: About 9.8 cm. Width: About 4.6 cm. Shape: Elongated oblong. Apex: Acute to cuspidate. Base: Cordate. Margin: Entire. Texture: Rugose, leathery, durable; both surfaces, very fine dense pubescence. Luster: Upper surface, glossy; lower surface, dull. Venation pattern: Pinnate. Petiole length: About 1.3 cm. Petiole diameter: About 3 mm. Color: Young and fully expanded foliage, upper surface: Dark green, darker than 147A. Young and fully expanded foliage, lower surface: Green, 147B. Petiole: Light green, 144B.

Flower description:

*Flower type and habit.*—Single salverform flower; terminal or axillary; flowers face mostly outward. Flowers self-cleaning. Freely flowering, more than 30 flowers per plant develop during the flowering season.

*Natural flowering season.*—Spring until frost in the autumn; flowering continuous.

*Flower longevity on the plant.*—About one week.

*Fragrance.*—Faint, sweet.

*Flowers.*—Appearance: Flared trumpet, corolla fused, five parted; flowers star-shaped; iridescent. Diameter: About 10.7 cm. Depth (length): About 5.1 cm. Corolla tube length: About 4.6 cm. Throat diameter: About 2.1 cm. Tube diameter, base: About 4 mm.

*Flower buds* (*just before opening*).—Length: About 6.7 mm. Diameter: About 1.6 cm. Shape: Oblong. Color: Red purple, 57A.

*Corolla.*—Arrangement/appearance: Single whorl of five petals, fused into flared trumpet; overlapping. Petal length: About 8.3 cm. Petal width: About 4.7 cm. Petal shape: Roughly spatulate. Petal apex: Acute to cuspidate. Petal margin: Entire; undulate, ruffled appearance. Petal texture: Smooth, velvety. Color: Petal, upper surface, when opening and fully opened: At temperatures greater than 29° C.: Red, richer than but closest to 45A to 45B; color fading to richer than but closest to 45B. At temperatures less than 29° C.: Dark pink, close to 58B or darker than 58B. Petal, lower surface, when opening and fully opened: At temperatures greater than 29° C.: Red, 45A to 45B. At temperatures less than 29° C.: Dark pink, close to 58B to 58C. Tube, fully opened: Red, 45A to 46A; towards base, white, 155D. Throat, fully opened: Base, white, 155D; mid-section, white, 155D, and red to red purple, 45A to 57A, longitudinal stripes; towards apex, white, 155D, and faint light yellow, close to 4C to 4D, longitudinal stripes.

*Sepals.*—Arrangement/appearance: Five per flower in a single whorl; fused, campanulate; reflexed. Length: About 1.1 cm. Width: About 3 mm. Shape: Elongated, linear. Apex: Sharply acute. Margin: Entire. Texture: Smooth, slightly waxy. Color, upper and lower surfaces: Light green, 144B to 144C.; towards apex, dark red, 53A.

*Peduncles.*—Length: About 1.75 cm. Diameter: About 2.5 mm. Angle: Twisted. Strength: Flexible, but strong. Color: Initially green, 144A, then dark red, 46A to 53A.

*Reproductive organs.*—Stamens: Quantity: Five; filaments fused to corolla. Anther shape: Oblong, elongated. Anther size: About 5 mm by 1 mm. Anther color: Light yellow, 10C to 10D. Pollen: None observed. Pistils: Quantity: One. Pistil length: About 1.7 cm. Stigma shape: Rounded. Stigma color: White, close to 155D. Style color: White, close to 155D. Ovary color: White, close to 155D.

*Seed.*—Seed production has not been observed.

Disease resistance: Plants of the new Mandevilla have not been noted to be resistant to pathogens common to Mandevilla.

Weather tolerance: Plants of the new Mandevilla have been observed to be tolerant to rain and wind and tolerant to temperatures from 1 to higher than 43° C.

It is claimed:

1. A new and distinct cultivar of Mandevilla plant named 'Red Velvet Petite', as illustrated and described.

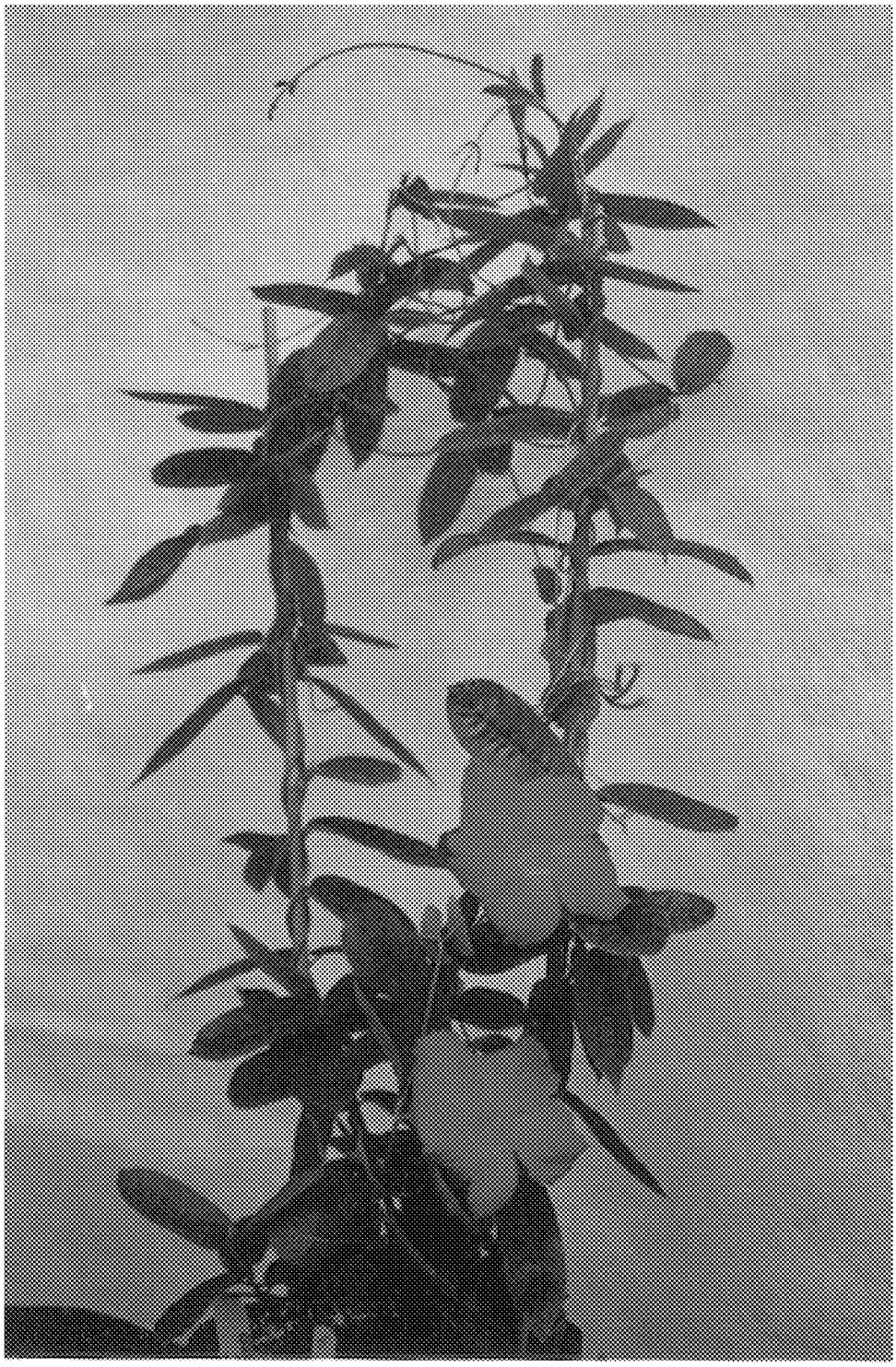

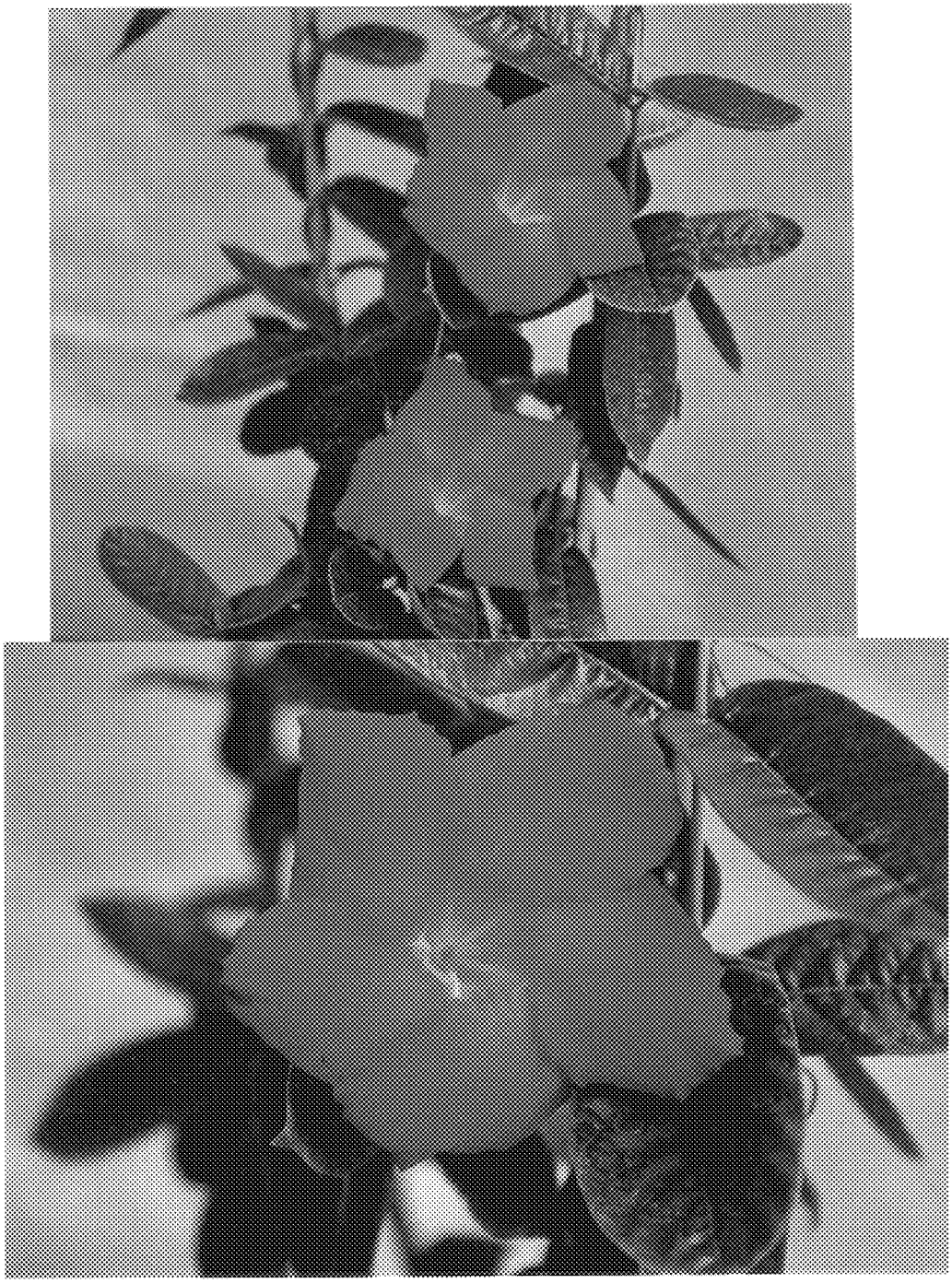

* * * * *